United States Patent [19]

Schefczik et al.

[11] Patent Number: 5,101,028
[45] Date of Patent: Mar. 31, 1992

[54] (1,2,4) TRIAZOLO (2,3-A) PYRIDINES

[75] Inventors: Ernst Schefczik, Ludwigshafen; Helmut Reichelt, Neustadt, both of Fed. Rep. of Germany

[73] Assignee: BASF Aktiengesellschaft, Ludwigshafen, Fed. Rep. of Germany

[21] Appl. No.: 565,098

[22] Filed: Aug. 10, 1990

[30] Foreign Application Priority Data

Aug. 12, 1989 [DE] Fed. Rep. of Germany ....... 3926770

[51] Int. Cl.$^5$ .................. C07D 413/04; C07D 471/04
[52] U.S. Cl. .................................... 544/127; 544/300; 544/354; 544/362; 546/119; 546/120
[58] Field of Search ................ 546/119, 120; 544/127, 544/300, 354, 362

[56] References Cited

U.S. PATENT DOCUMENTS 4,288,438 9/1981 Kubo et al. .................... 546/120

FOREIGN PATENT DOCUMENTS 2351978 12/1977 France .

OTHER PUBLICATIONS

Synthesis, 1986, pp. 860-862, R. C. Phadke et al., "A Novel, One-Step Synthesis of [1,2,4]Triazolo[1,5-A]-Pyridine Derivatives".
Synthesis, Nr. 10, Oktober 1986, Seiten 860-862, Stuttgart, DE; D. W. Rangnekar et al.: "A Novel, One-Step Synthesis of [1,2,4]Triazolo[1,5-a]-Pyridine Derivatives", *Das ganze Dokument*.

Primary Examiner—Bernard Dentz
Attorney, Agent, or Firm—Oblon, Spivak, McClelland, Maier & Neustadt

[57] ABSTRACT

Triazolopyridines of the formula

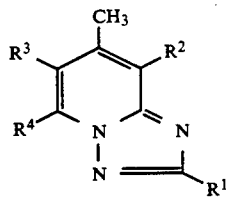

where
$R^1$ is $C_1$–$C_{20}$-alkyl which may be substituted, phenyl which may be substituted, or hydroxyl,
$R^2$ is hydrogen, formyl, nitroso, cyano or substituted methyl,
$R^3$ is hydrogen, cyano, carbamoyl, carboxyl or $C_1$–$C_4$-alkoxycarbonyl and
$R^4$ is hydroxyl, halogen, amino which may be substituted or the radical of a compound with an acidic CH, are prepared as described. The compounds are useful as intermediates in the preparation of dyes.

2 Claims, No Drawings

(1,2,4) TRIAZOLO (2,3-A) PYRIDINES

The present invention relates to novel triazolopyridines of the formula I

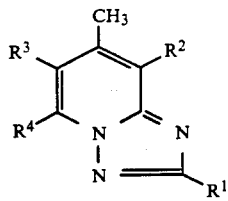

(I)

where
- $R^1$ is $C_1-C_{20}$-alkyl which may be substituted and may be interrupted by one or more oxygens, phenyl which may be substituted, or hydroxyl,
- $R^2$ is hydrogen, formyl, nitroso, cyano, $C_1-C_4$-alkoxymethyl or $CH_2-NL^1L^2$ where $L^1$ and $L^2$ are identical or different and each, independently of one another, is hydrogen or $C_1-C_4$-alkyl, or they form together with the nitrogen connecting them a 5- or 6-membered saturated heterocylic radical,
- $R^3$ is hydrogen, cyano, carbamoyl, carboxyl or $C_1-C_4$-alkoxycarbonyl and
- $R^4$ is hydroxyl, halogen, $-NL^1L^2$ where $L^1$ and $L^2$ each has the abovementioned meaning, or the radical of a compound with an acidic CH, and to a process for the preparation of 2-substituted 5-methyl-4- or 6-cyano-7-hydroxy[1,2,4]triazolo[2,3-a]-pyridines.

Synthesis (1986) pages 860-862 discloses 4-cyano-5,7-dimethyl[1,2,4]triazolo[2,3-a]pyridines which are unsubstituted or substituted in position 2 by methyl, phenyl, styryl or 3-coumarinyl. However, it has emerged that these triazolopyridines have little suitability for subsequent reactions because they have no functional groups on the pyridine ring apart from the cyano group.

It was therefore an object of the present invention to provide novel triazolopyridines which have additional functional groups on the pyridine ring and can be prepared in a straightforward manner.

We have accordingly found the triazolopyridines of the formula I defined in the first paragraph.

The IUPAC name of the parent molecule from which the novel triazolopyridines of the formula I are derived is [1,2,4]triazolo[2,3-a]pyridine, with the rings being numbered as follows

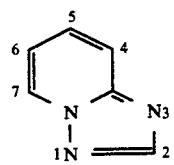

The compounds of the formula I can exist in several tautomeric forms, all of which are embraced by the patent claim. For example, the compounds with $R^4$=hydroxyl can exist in the following tautomeric forms, inter alia:

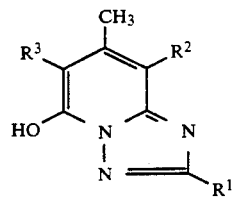

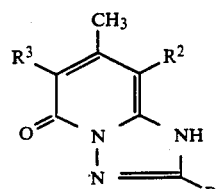

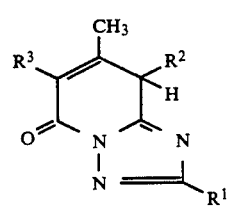

When $R^1$ in the formula I is substituted $C_1-C_{20}$-alkyl, examples of suitable substituents are phenyl, phenoxy, carboxyl or $C_1-C_{20}$-alkoxycarbonyl whose alkyl chain may be interrupted by 1 to 4 oxygens and/or substituted by phenyl or phenoxy.

When $R^1$ in the formula I is alkyl which is interrupted by oxygens, the preferred alkyl radicals are interrupted by 1 to 4 oxygens, in particular 1 or 2 oxygens.

When $R^1$ in the formula I is substituted phenyl, examples of suitable substituents are $C_1-C_4$-alkyl, $C_1-C_4$-alkoxy, halogen, especially chlorine or bromine, or nitro or carboxyl.

When $R^4$ in the formula I is the radical of a compound with an acidic CH, this radical can be derived from e.g. nitromethane, nitroethane or compounds of the formulae V to X where X$^1$ is cyano, nitro, C$_1$–C$_4$-alkanoyl, benzoyl which may be substituted by C$_1$–C$_4$-alkyl, C$_1$–C$_4$-alkoxy or halogen, or C$_1$–C$_4$-alkylsulfonyl, or phenylsulfonyl which may be substituted by C$_1$–C$_4$-alkyl, C$_1$–C$_4$-alkoxy or halogen, or carboxyl, C$_1$–C$_4$-alkoxycarbonyl, phenoxycarbonyl, carbamoyl, mono- or di-C$_1$–C$_4$-alkylcarbamoyl, or phenylcarbamoyl which be substituted by C$_1$–C$_4$-alkyl, C$_1$–C$_4$-alkoxy or halogen, or phenyl which may be substituted by C$_1$–C$_4$-alkyl, C$_1$–C$_4$-alkoxy, halogen or nitro, or 2-benzothiazolyl, 2-benzimidazolyl, 5-phenyl-1,3,4-thiadiazol-2-yl or 2-hydroxy-3-quinoxalinyl, X$^2$ is C$_1$–C$_4$-alkyl or C$_1$–C$_4$-alkoxy, X$^3$ is C$_1$–C$_4$-alkoxycarbonyl, phenylcarbamoyl or 2-benzidazolyl, X$^4$ is hydrogen or C$_1$–C$_4$-alkyl, X$^5$ is hydrogen, C$_1$–C$_4$-alkyl or phenyl and X$^6$ is C$_1$–C$_4$-alkyl.

Particularly suitable compounds with an acidic CH are those of the formulae V, VI and VIII, where X$^1$ is cyano, acetyl, benzoyl, C$_1$–C$_4$-alkoxycarbonyl, phenoxycarbonyl, mono-C$_1$–C$_2$-alkylcarbonyl, phenylcarbamoyl, phenyl, 2-benzimidazolyl, 2-benzothiazolyl or 5-phenyl-1,3,4-thiadiazol-2-yl, X$^2$ is C$_1$–C$_2$-alkoxy, X$^3$ is C$_1$–C$_2$-alkoxycarbonyl or phenylcarbamoyl and X$^4$ is methyl.

Examples of R$^1$ are hydrogen, methyl, ethyl, propyl, isopropyl, butyl, isobutyl, sec-butyl, pentyl, isopentyl, neopentyl, tert-pentyl, hexyl, heptyl, 1-ethylpentyl, octyl, isooctyl, 2-ethylhexyl, nonyl, isononyl, decyl, isodecyl, undecyl, dodecyl, tridecyl, isotridecyl, tetradecyl, pentadecyl, hexadecyl, heptadecyl, octadecyl, nonadecyl, eicosyl (isooctyl, isononyl, isodecyl and isotridecyl are trivial names deriving from the alcohols obtained in the oxo synthesis—cf. Ullmanns Enzyklopädie der technischen Chemie, 4th edition, volume 7, pages 215 to 217, and volume 11, pages 435 and 436), 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl, 3,6,9-trioxaundecyl, 3,6,9,12-tetraoxatridecy, 1,3,6,9,12-tetraoxatetradecy1,2-carboxyethyl, 2-methoxycarbonylethyl, benzyl, 1- or 2-phenylethyl, 3-benzyloxypropyl, phenoxymethyl, 6-phenoxy-4-oxahexyl, 8-phenoxy-4-oxaoctyl, 2-, 3- or 4-methylphenyl, 2-, 3- or 4-methoxyphenyl, 2-, 3- or 4-chlorophenyl, 2-, 3- or 4-nitrophenyl or 2-, 3- or 4-carboxylphenyl.

Examples of R$^2$ are aminomethyl, N-mono- or N,N-dimethylaminomethyl, N-mono- or N,N-diethylaminomethyl, N-mono- or N,N-dipropylaminomethyl, morpholinomethyl, methoxymethyl, ethoxymethyl, propoxymethyl, isopropoxymethyl or butoxymethyl.

Examples of R$^3$ are methoxycarbonyl, ethoxycarbonyl, propoxycarbonyl, isopropoxycarbonyl, butoxycarbonyl, isobutoxycarbonyl or sec-butoxycarbonyl.

Examples of R$^4$ are amino, mono- or dimethylamino, mono- or diethylamino, mono- or dipropylamino, mono- or diisopropylamino, mono- or dibutylamino, pyrrolidino, piperidino, morpholino, piperazino or N-(C$_1$–C$_4$-alkyl)-piperazino.

Preferred triazolopyridines of the formula I are those in which R$^3$ is cyano.

Another object of the present invention was to provide a process to prepare in a straightforward manner 2-substituted 5-methyl-6-cyano-7-hydroxy[1,2,4]-triazolo-[2,3-a]pyridines.

We have now found that the triazolopyridines of the formula IIa

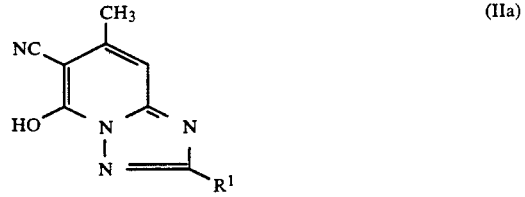

where

R$^1$ is C$_1$–C$_{20}$-alkyl which may be substituted and may be interrupted by one or more oxygens, phenyl which may be substituted, or hydroxyl, are advantageously prepared by reacting 3-aminocrotonitrile with a hydrazine of the formula III $$A-CO-NH-NH-CO-CH_2CN \quad (III)$$

where

A is amino or the abovementioned radical R$^1$, in the presence or absence of a dehydrating agent at from 100° to 200° C.

The reaction generally takes place in an inert organic solvent. Examples of such solvents are haloalkanes such as dichloromethane, chloroform, dichloroethane or trichloroethane, halobenzenes such as chlorobenzene, bromobenzene or o-dichlorobenzene, higher alkanols such as pentanol, hexanol, heptanol, octanol or 2-ethylhexanol, ethers such as ethylene glycol monomethyl or monoethyl ether, formamide or N-methylpyrrolidone.

The molar ratio of aminocrotonitrile to hydrazine III is generally 1:1 to 2:1, preferably 1.25:1.

It is advantageous in some cases to carry out the reaction in the presence of a dehydrating agent. Examples of suitable dehydrating agents are carboxylic anhydrides such as acetic anhydride, or Lewis acids, e.g. zinc chloride.

1 to 2 mol of dehydrating agent are generally used per mol of hydrazine III.

The process according to the invention is normally carried out at from 100° to 200° C.

After the reaction is complete, which generally takes 2 to 8 hours, the target product IIa is normally in the form of a precipitate and can be filtered off and further purified if necessary.

We have also found that triazolopyridines of the formula IIb

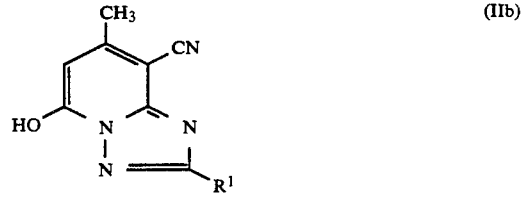

where
R$^1$ is C$_1$-C$_{20}$-alkyl which may be substituted or may be interrupted by one or more oxygens, phenyl which may be substituted, or hydroxyl, are advantageously prepared by reacting a hydrazine of the formula IV $$A-CO-NH-NH-CO-CH_2COCH_3 \quad (IV)$$

where
A is amino or the abovementioned radical R$^1$, in a basic medium with malononitrile and subsequently treating with acid.

The process according to the invention is expediently carried out in an alcohol, e.g. methanol or ethanol. Examples of basic media are alkali metal alkanolates such as sodium methanolate or sodium ethanolate.

The reaction is usually carried out at from 50 to 120° C. and, when complete, the mixture is discharged into water which is then neutralized.

It is advisable to precede the acid treatment, which is normally carried out in acetic acid, by isolation of the precipitated product. The acid treatment is normally carried out at from 80° to 120° C.

The hydrazine derivative of the formula IV can be obtained from diketene and the hydrazine of the formula XI $$A-CO-NH-NH_2 \quad (XI)$$

where A has the abovementioned meaning.

The other triazolopyridines of the formula I can be prepared in a conventional manner from the 4- or 6-cyano-7-hydroxytriazolopyridines of the formula IIa or IIb.

For example, the substituent R$^2$ can be introduced by an electrophilic substitution reaction, e.g. Vilsmeier reaction, or nitrosation, with or without subsequent derivatization.

The cyano group in position 6 can be converted by conventional methods into carbamoyl, carboxyl or C$_1$-C$_4$-alkoxycarbonyl.

The hydroxyl in position 7 can be replaced by halogen by treatment with acid halides, especially acid chlorides, e.g. phosphorus oxytrichloride.

It is possible in turn to replace the halogen atom by reaction, by conventional methods, with compounds with an acidic CH or amines of the formula XII

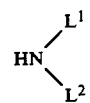
(XII)

where L$^1$ and L$^2$ each has the abovementioned meaning.

The novel triazolopyridines of the formula I are valuable intermediates for the synthesis of dyes and active substances.

The examples which follow are intended to illustrate the invention in detail.

EXAMPLE 1

(6-Cyano-2,5-dimethyl-7-hydroxy[1,2,4]triazolo[2,3-a]pyridine)

120 g of 3-aminocrotonitrile were introduced into 250 ml of anhydrous chlorobenzene and stirred at 110 to 120° C. Then 141 g of N-acetyl-N,-cyanoacetylhydrazine were introduced a little at a time, waiting after each addition until the exothermic reaction had subsided. The reaction mixture was then boiled for 2 hours and, after addition of 125 g of acetic anhydride, refluxed for a further 2 hours. The heating was then switched off; 500 ml of methanol were added at 60° to 70° C., and the mixture was allowed to cool to room temperature. The resulting suspension was filtered with suction, and the residue was washed with methanol and dried at 80° 140 g of 6-cyano-2,5-dimethyl-7-hydroxy[1,2,4]triazolo[2,3-a]-pyridine were obtained as a colorless powder which did not melt up to 350°. The compound dissolves in dilute aqueous alkalies and, after recrystallization from N-methylpyrrolidone, showes the following analysis:

C$_9$H$_8$N$_4$O (188); calc.: C 57.4, H 4.3, N 29.8, O 8.5, found: 57.4, 4.4, 29.5, 9.9

EXAMPLE 2

(6-Cyano-2-(1-ethylpentyl)-7-hydroxy-5-methyl[1,2,4]-triazolo[2,3-a]pyridine)

A mixture of 750 ml of n-pentanol, 120 g of 3-aminocrotonitrile and 225 g of N-cyanoacetyl-N'-(2-ethylhexanoyl)hydrazine was refluxed for 2 hours. Addition of 150 g of anhydrous zinc chloride was followed by boiling for a further 4 hours. Then 200 ml of concentrated hydrochloric acid were added, and the pentanol was removed by steam distillation. The remaining suspension was filtered with suction, and the residue was washed with water and dried at 80° C. under reduced pressure. 265 g of 6-cyano-2-(1-ethylpentyl)-7-hydroxy-5-methyl-[1,2,4]triazolo[2,3-a]pyridine were obtained as a colorless powder. A sample recrystallized from acetic acid has a melting point of 253° to 254° C. and the following analysis:

C$_{15}$H$_{20}$N$_4$O (272); calc.: C 66.2, H 7.4, N 20.6, O 5.9, found: 66.0, 7.5, 20.7, 5.9

EXAMPLE 3

(6-Cyano-2,7-dihydroxy-5-methyl[1,2,4]triazolo[2,3-a]pyridine)

115 g of 3-aminocrotonitrile and 142 g of N-carbamoyl-N'-cyanoacetylhydrazine were introduced into 1000 ml of n-pentanol. The mixture was heated to boiling within one hour and refluxed for 6 hours. After cooling, the suspension was filtered with suction, and the residue was washed with methanol. Drying resulted in 134 g of 6-cyano-2,7-dihydroxy-5-methyl[1,2,4]-triazolo[2,3-a]pyridine as the ammonium salt, which does not melt up to 350° C. A sample recrystallized from water has the following analysis:

C$_8$H$_9$N$_5$O$_2$(207); calc.: C 46.3, H 4.4, N 33.8, O 15.5, found: 46.2, 4.4, 33.4, 15.7

EXAMPLE 4

(6-Cyano-7-hydroxy-5-methyl-2-phenoxymethyl[1,2,4]-triazolo[2,3-a]pyridine)

125 g of 3-aminocrotonitrile were introduced into 250 ml of anhydrous o-dichlorobenzene and stirred at 100° C. To this were added 233 g of N-cyanoacetyl-N'-phenoxyacetylhydrazine a little at a time, and the mixture was then stirred at 140° C. for 2 hours. 120 g of acetic anhydride were added and the mixture was then refluxed for 2 hours and, while cooling, 500 ml of methanol were added. After cooling, the precipitate was filtered off with suction, washed with methanol and dried at 80° C. under reduced pressure. 213 g of 6-cyano-7-hydroxy-5-methyl-2-phenoxymethyl[1,2,4]-triazolo[2,3-a]-pyridine were obtained as a colorless powder. A sample recrystallized from γ-butyrolactone does not melt up to 350° C. and has the following analysis:

$C_{15}H_{12}N_4O_2$ (280) calc.: C 64.3, H 4.3, N 20.0, O 11.4, found: 64.0, 4.4, 20.0, 11.8

EXAMPLE 5

(2-Benzyl-6-cyano-7-hydroxy-5-methyl[1,2,4]-triazolo[2,3-a]pyridine)

120 g of 3-aminocrotonitrile were dissolved in 750 ml of ethylene glycol monoethyl ether at 50° to 100° C. To this were added 217 g of N-cyanoacetyl-N,-phenylacetylhydrazine, and the mixture was refluxed for 8 hours. After cooling, it was poured into 1200 ml of water and 150 ml of concentrated hydrochloric acid, when the reaction product precipitated. Filtration with suction, washing with water and drying at 80° C. under reduced pressure resulted in 184 g of 2-benzyl-6-cyano-7-hydroxy-5-methyl[1,2,4]triazolo[2,3-a]pyridine as a colorless powder. A sample recrystallized from acetic acid/N,N-dimethylformamide (3:1 v/v) has a melting point of 319° to 320° C. and the following analysis:

$C_{15}H_{12}N_4O$ (264); calc.: C 68.2, H 4.6, N 21.2, O 6.1, found: 68.1, 4.6, 21.2, 6.1.

EXAMPLE 6

(2-Carboxyethyl-6-cyano-7-hydroxy-5-methyl[1,2,4]-triazolo[2,3-a]pyridine)

150 g of 3-aminocrotonitrile were dissolved in 750 ml of n-pentanol and stirred at 100° C. To this were added 199 g of N-(3-carboxypropionyl)-N,-cyanoacetylhydrazine a little at a time, and the mixture was refluxed for 2 hours. 175 g of anhydrous zinc chloride were added and the mixture was boiled for a further 4 hours and then 200 ml of concentrated hydrochloric acid were run in. The n-pentanol was removed by steam distillation, and the solid was filtered off with suction and washed with water. Drying at 80° C. under reduced pressure resulted in 121 g of 2-carboxyethyl-6-cyano-7-hydroxy-5-methyl[1,2,4]triazolo[2,3-a]pyridine as a colorless powder which is readily soluble in aqueous ammonia. A sample recrystallized from 7-butyrolactone melts at 304 to 305° C. and has the following analysis:

$C_{11}H_6hd 10N_4O_3$ (246); calc.: C 53.7, H 4.1, N 22.7, O 19.5, found: 53.5, 4.2, 22.4, 19.9

EXAMPLE 7

(6-Cyano-2-ethyl-7-hydroxy-5-methyl[1,2,4]-triazolo[2,3-a]pyridine]

125 g of 3-aminocrotonitrile were dissolved in 500 ml of formamide and heated to 100° C. To this were added 155 g of N-cyanoacetyl-N,-propionylhydrazine in such a way that the exothermic reaction had subsided before the next addition. The mixture was then stirred at 120° to 125° C. for 6 hours and allowed to cool. It was then diluted with 1000 ml of water and acidified with concentrated hydrochloric acid. Filtration with suction, washing with water and drying at 100° C. resulted in 141 g of 6-cyano-2-ethyl-7-hydroxy-5-methyl[1,2,4]-triazolo-[2,3-a]pyridine. A sample recrystallized from N-methylpyrrolidone melts at 346° to 348° C. and has the following analysis:

$C_{10}H_{10}N_4O$ (202); calc.: C 59.4, H 5.0, N 27.7, O 7.9, found: 59.2, 5.0, 27.8, 8.3

EXAMPLE 8

(6-Cyano-2-heptadecyl-7-hydroxy-5-methyl[1,2,4]-triazolo-[2,3-a]pyridine)

A mixture of 1000 ml of ethylene glycol monoethyl ether, 120 g of 3-aminocrotonitrile and 365 g of N-cyanoacetyl-N'-stearoylhydrazine was heated to 135° C. within 2 hours and then refluxed for a further 2 hours. Addition of 150 g of anhydrous zinc chloride and boiling for a further 4 hours were followed by dilution of the melt with 2000 ml of water and addition of 200 ml of 12 % by weight hydrochloric acid. The precipitated product was filtered off with suction, washed with water and dried at 80° C. under reduced pressure. 397 g of 6-cyano-2-heptadecyl-7-hydroxy-5-methyl[1,2,4]-triazolo[2,3-a]pyridine were obtained. The compound melts at 274 to 275° C. after recrystallization from acetic acid and has the following analysis:

$C_{25}H_{40}N_4O$ (412); calc.: C 72.8, H 9.8, N 13.6, O 3.9, found: 72.5, 9.8, 13.5, 4.2

EXAMPLE 9

(6-Cyano-7-hydroxy-5-methyl-2-(p-nitrophenyl)[1,2,4]-triazolo[2,3-a]pyridine)

A mixture of 2000 ml of n-pentanol, 125 g of 3-aminocrotonitrile and 248 g of N-cyanoacetyl-N,-(p-nitrobenzoyl)hydrazine was refluxed for 2 hours and, after addition of 150 g of anhydrous zinc chloride, boiled for a further 2 hours. Then 150 ml of concentrated hydrochloric acid were added and the n-pentanol was removed by steam distillation. The resulting suspension was filtered hot with suction, and the residue was washed with water and dried at 100° C. 256 g of 6-cyano-7-hydroxy-5-methyl-2-(p-nitrophenyl)[1,2,4]-triazolo[2,3-a]-pyridine were obtained. The compound does not melt up to 350° C. and has the following analysis (recrystallized from N-methylpyrrolidone):

$C_{14}H_9N_5O_3$ (295); calc.: C. 56.9, H 3.1, N 23.7, O 16.3, found: 57.9, 3.3, 23.4, 16.2

EXAMPLE 10

6-Cyano-7-hydroxy-5-methyl-2-(m-nitrophenyl)-[1,2,4]triazolo[2,3-a]pyridine was obtained in a similar manner to Example 9 and likewise does not melt up to 350°.

EXAMPLE 11

(6-Cyano-2-(1-ethylpentyl)-4-formyl-7-hydroxy-5-methyl-[1,2,4]triazolo[2,3-a]pyridine)

120 g of N,N-dimethylformamide and 272 g of 6-cyano-2-(1-ethylpentyl)-7-hydroxy-5-methyl[1,2,4]-triazolo[2,3-a]pyridine were introduced into 1000 ml of chloroform and stirred at room temperature. To this were added dropwise 250 g of phosphorus oxytrichloride, and the mixture was then refluxed for 6 hours. 250 ml of water were then added and the chloroform was removed by steam distillation. The remaining suspension was filtered with suction, and the residue was washed with water and dried at 80° C. under reduced pressure. 265 g of the compound of the formula

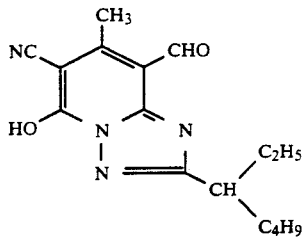

were obtained with a melting point of 214° to 215° C. (from ethanol).

Analysis:

$C_{16}H_{20}N_4O_2$ (300); calc.: C 64.0, H 6.7, N 18.6, O 10.7, found: 64.0, 6.9, 18.6, 10.8

The following compounds of the formula

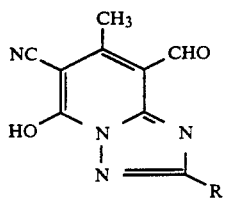

were obtained in a similar manner to Example 11.

| Ex. No. | R | M.p. | (recrystallized from) |
|---------|---|------|----------------------|
| 12 | $CH_3$ | 336–337° C. | (N-methyl-pyrrolidone) |
| 13 | $(CH_2)_{16}CH_3$ | 205–206° C. | (n-pentanol) |

EXAMPLE 14

(7-Chloro-6-cyano-2-(1-ethylpentyl)-5-methyl[1,2,4]-triazolo[2,3-a]pyridine 272 g of 6-cyano-2-(1-ethylpentyl)-7-hydroxy-5-methyl[1,2,4]triazolo[2,3-a]pyridine were introduced into 250 g of phosphorus oxytrichloride and stirred at 105° C. for 4 hours. Then 250 g of methanol were added dropwise, the mixture was briefly boiled and 250 ml of water were run in. The solution was cooled and, at 10° to 20° C., the pH was adjusted to 7.5 with aqueous ammonia, when the target product precipitated. It was filtered off with suction, washed with water and dried at 50° C. under reduced pressure. 264 g of the compound of the formula

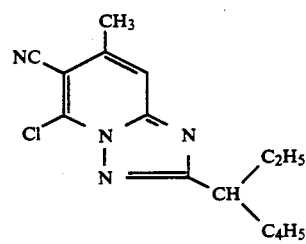

were obtained. A sample recrystallized from ethanol/-cyclohexane has a melting point of 95° to 96° C. and the following analysis:

$C_{15}H_{19}ClN_4$ (209.5) calc.: C 62.0, H 6.6, N 12.2, O 19.3, found: 62.0, 6.7, 12.0, 19.2

The following compounds of the formula

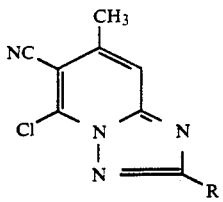

were obtained in a similar manner to Example 14.

| Ex. No. | R | M.p. (recrystallized from) | Cl calc. | Cl found |
|---------|---|----------------------------|----------|----------|
| 15 | $CH_3$ | 202–203° C. (acetic acid) | 17.2 | 16.9% |
| 16 | $C_2H_5$ | 162–163° C. (ethanol) | 16.8 | 16.5% |
| 17 | $C_6H_5CH_2$ | 177–178° C. (n-pentanol) | 12.5 | 12.2% |
| 18 | $C_6H_5OCH_2$ | 187–188° C. (acetic acid) | 11.9 | 11.8% |
| 19 | $C_{17}H_{19}$ | 110° C. (ethanol) | 8.3 | 8.2% |

EXAMPLE 20

(2-Benzyl-6-cyano-7-dimethylamino-5-methyl[1,2,4]-triazolo[2,3-a]pyridine)

282.5 g of the compound obtained as in Example 17 in 1000 ml of ethanol were heated to boiling. To this were added dropwise 300 g of 40 % by weight aqueous dimethylamine solution within one hour, and the mixture was then refluxed for 6 hours. During this the starting material completely dissolved, and the final product crystallized during cooling. Filtration with suction and drying resulted in 270 g of the compound of the formula

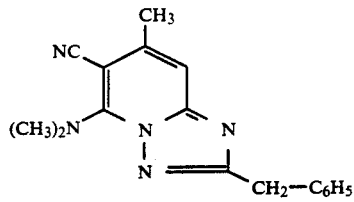

with a melting point of 130° to 131° C. (from ethanol).

Analysis:

$C_{17}H_{17}N_5$ (291) calc.: C 70.1, H 5.9, N 24.0, found: 70.0, 6.0, 24.2

The following compounds of the formula

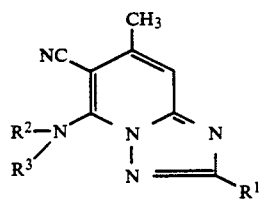

were obtained in a similar manner to Example 20.

| Ex. No. | $R^1$ | $R^2$ | $R^3$ | M.p. (recrystallized from) | | C | H | N | O |
|---|---|---|---|---|---|---|---|---|---|
| 21 | $CH_3$ | $CH_3$ | $CH_3$ | 153–154° C. (ethanol) | calc.: found: | 61.4 61.5 | 6.1 6.2 | 32.5 32.4 | — — |
| 22 | $CH_3$ | $C_2H_5$ | $C_2H_5$ | 86–87° C. (cyclohexane/ethanol) | calc.: found: | 64.2 64.4 | 7.0 7.0 | 28.8 28.8 | — — |
| 23 | | $(CH_2)_2O(CH_2)_2$ | | 90–91° C. (methanol) | calc.: found: | 66.8 67.1 | 8.0 8.2 | 20.5 20.4 | 4.7 4.8 |
| 24 | $C_6H_5CH_2$ | $CH_3$ | $CH_2CH_2OH$ | 119–120° C. (ethanol) | calc.: found: | 67.3 67.3 | 6.0 6.1 | 21.8 21.7 | 5.0 5.2 |
| 25 | $C_6H_5CH_2$ | $(CH_2)_2O(CH_2)_2$ | | 131–132° C. (ethanol) | calc.: found: | 68.5 68.5 | 5.7 6.0 | 21.0 20.9 | 4.8 5.1 |

EXAMPLE 26

14.5 g of the compound described in Example 14 were heated with 9.9 g of malononitrile and 15.3 g of triethylamine in 300 ml of N,N-dimethylformamide at 90° C. for 5 hours. The mixture was then poured into 1.5 l of water, concentrated hydrochloric acid was added to pH 5, the precipitate was filtered off with suction, washed with water and dried at 50° C. under reduced pressure. 13.5 g of the compound of the formula

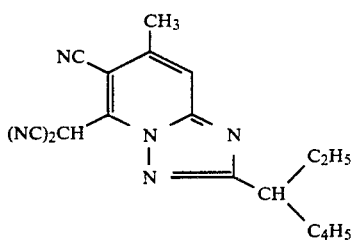

were obtained. A sample recrystallized from ethanol has a melting point of 231° to 232° C. and the following analysis:

$C_{18}H_{20}N_6$ (320.4); calc.: C 67.5, H 6.3, N 26.2, found: 67.1, 6.4, 26.2

The following compounds of the formula

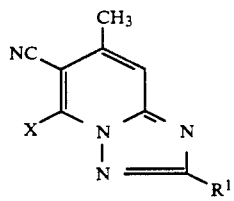

were obtained in a similar manner to Example 26.

solution was added to neutralize, and the precipitate was filtered off with suction, washed with water and dried at 50° C. under reduced pressure. 1.8 g of the compound of the formula

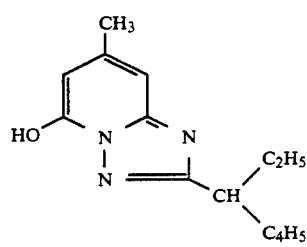

were obtained. A sample recrystallized from ethanol has a melting point of 194° C. and the following analysis:

$C_{14}H_{21}N_3O$ (247.3); calc. C 68.0, H 8.6, N 17.0, O 6.5. found: 67.6, 8.7, 16.9, 6.7

EXAMPLE 31

(6-Cyano-2-(1-ethylpentyl)-7-hydroxy-5-methyl-4-nitroso-[1,2,4]triazolo[2,3-a]pyridine)

5.44 g of the compound described in Example 2 were dissolved in 30 ml of glacial acetic acid and 30 ml of concentrated hydrochloric acid. At 0 to 5° C., 1.45 g of sodium nitrite dissolved in 5 ml of water were added dropwise. The mixture was stirred at this temperature for 2 hours. It was then poured into 300 ml of water, stirred for 30 minutes, and the precipitate was filtered off with suction and dried. 3.7 g of 6-cyano-2-(1-ethylpentyl)-7-hydroxy-5-methyl-4-nitroso[1,2,4]-triazolo[2,3-a]pyridine were obtained as a green powder. A sample recrystallized from toluene melts at 129° to 130° C. and has the following analysis:

$C_{15}H_{19}N_5O_2$ (301.4); calc.: C 59.8, H 6.4, N 23.2, O

| Ex. No. | $R^1$ | X | M.p. (recryst. from) | Analysis | | | | |
|---|---|---|---|---|---|---|---|---|
| 27 | $(CH_2)_{16}CH_3$ | $CH(CN)_2$ | 245–248° C. (ethanol) | calc.: found: | $C_{28}H_{40}N_6$ (460.7) C 73.0 72.3 | H 8.8 8.8 | N 18.2 18.1 | |
| 28 | $(CH_2)_{16}CH_3$ | | 97–98° C. (ethanol) | calc.: found: | $C_{32}H_{49}N_5O_2$ (535.8) C 71.7 71.5 | H 9.2 9.4 | N 13.1 12.7 | O 6.0 6.1 |
| 29 | $CH(C_2H_5)C_4H_9$ | | 122–124° C. (ethanol/$H_2O$) | calc.: found: | $C_{21}H_{30}N_6O_5 \cdot 2H_2O$ (446.5) C 56.5 56.7 | H 6.8 7.1 | N 18.8 8.4 | O 17.9 17.9 |

EXAMPLE 30

2.72 g of the compound described in Example 2 in 30 ml of 60 % by weight sulfuric acid were heated at 120° C. for 10 hours. The mixture was then poured into 300 ml of ice-water, 50 % by weight sodium hydroxide 10.6, found: 59.3, 6.5, 23.0, 10.8

The $^1$H-NMR spectrum is consistent with the structure.

EXAMPLE 32

(4-Cyano-7-hydroxy-5-methyl-2-phenyl[1,2,4]triazolo-[2,3-a]pyridine)

180 g of 30 % by weight methanolic sodium methylate solution were added dropwise to a mixture of 600 ml of methanol, 66 g of malononitrile and 220 g of N-benzoyl-N'-acetoacetylhydrazine. The reaction mixture was refluxed for 6 hours and then discharged into ice-water, and the mixture was neutralized by addition of 60 g of acetic acid. The precipitated colorless product was filtered off with suction, washed with water and dried. Yield: 248 g. The product was then introduced into 1000 ml of acetic acid and refluxed for 4 hours. The mixture was cooled and then diluted with the same volume of water, and the precipitate was filtered off with suction, washed with water and dried. 192 g of the compound of the formula

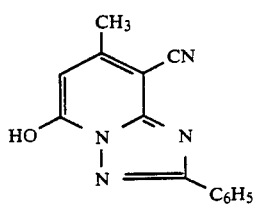

were obtained. A sample was recrystallized from N,N-dimethylformamide/acetic acid (1:1 v/v) and has a melting point of 342° to 343° C.

Analysis: $C_{14}H_{10}N_4O$ (250); calc.: C 67.1, H 4.0, N 22.4, O 6.4, found: 66.9, 4.0, 22.2, 6.7

EXAMPLE 33

(4-Cyano-7-chloro-5-methyl-2-phenyl[1,2,4]triazolo-[2,3-a]pyridine)

250 g of the compound obtained as in Example 32 were introduced into 500 ml of phosphorus oxytrichloride and refluxed for 6 hours. The reaction mixture was discharged into ice-water, and the precipitated product was filtered off with suction and washed with water. Drying resulted in 265 g of the colorless compound of the formula

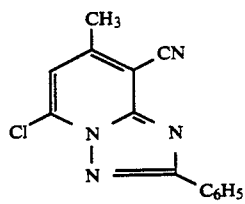

which, after recrystallization from acetic acid, had a melting point of 223° to 224° C. Chlorine calc.: 13.2, found: 13.1.

We claim:

1. A triazolopyridine of the formula I

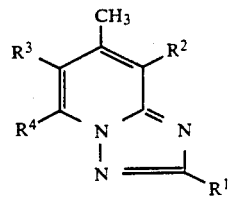

where
$R^1$ is $C_1$-$C_{20}$-alkyl optionally substituted with phenyl, phenoxy, carboxy or $C_1$-$C_6$hd 20-alkoxycarboxyl whose alkyl chain may be interrupted by 1 to 4 oxygens or substituted by phenyl or phenoxy, and may be interrupted by one or more oxygens, phenyl optionally substituted with $C_1$-$C_4$-alkyl, $C_1$-$C_4$-alkoxy, halogen, nitro or carboxyl, or hydroxyl,
$R^2$ is hydrogen, formyl, nitroso, cyano, $C_1$-$C_4$-alkoxymethyl or $CH_2$—$NL^1L^2$ where $L^1$ and $L^2$ are identical or different and each, independently of one another, is hydrogen or $C_1$-$C_4$-alkyl, or they form together with the nitrogen connecting them a 5- or 6-membered saturated heterocyclic radical,
$R^3$ is cyano, carbamoyl, carboxyl or $C_1$-$C_4$-alkoxycarbonyl and
$R^4$ is hydroxyl, halogen, —$NL^1L^2$ where $L^1$ and $L^2$ each have the abovementioned meaning, or the radical of a compound with an acidic CH derived from the nitromethane, nitroethane or compounds of the formulae V to X

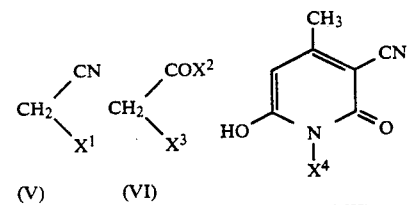

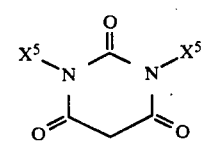

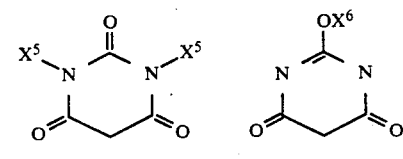

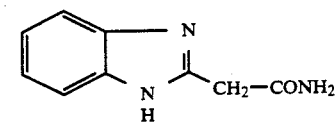

where
$X^1$ is cyano, nitro, $C_1$-$C_4$-alkanoyl, benzoyl optionally substituted by $C_1$-$C_4$-alkyl, $C_1$-$C_4$-alkoxy or halogen, $C_1$-$C_4$-alkylsulfonyl, phenylsulfonyl optionally substituted by $C_1$-$C_4$-alkyl, $C_1$-$C_4$-alkoxy or halogen, carboxyl, $C_1$-$C_4$-alkoxycarbonyl, phenoxycarbonyl, carbamoyl, momo- or di-$C_1$-$C_4$-alklcarbamoyl, phenylcarbamoyl optionally substituted by $C_1$-$C_4$-alkyl, $C_1$-$C_4$-alkoxy or halogen, phenyl optionally substituted by $C_1$-$C_4$-alkyl, $C_1$-$C_4$-alkoxy, halogen or nitro, 2-benzothiazolyl, 2-benzimidazolyl, 5-phenyl-1,3,4-thiadiazol-2-yl or 2-hydroxy-3-quinoxalinyl,
$X^2$ is $C_1$-$C_4$-alkoxy,
$X^3$ is $C_1$-$C_4$-alkoxycarbonyl, phenylcarbamoyl or 2-benzimidazolyl,
$X^4$ is hydrogen or $C_1$-$C_6$-alkyl,
$X^5$ is hydrogen, $C_1$-$C_4$-alkyl or phenyl and
$X^6$ is $C_1$-$C_4$-alkyl.

2. A triazolopyridine as claimed in claim 1, in which $R^3$ is cyano.

* * * * *